United States Patent [19]

Lin

[11] 4,106,698

[45] Aug. 15, 1978

[54] PERSONAL AUTOMATIC VAPORIZER

[75] Inventor: A. Oscar Lin, Woodside, N.Y.

[73] Assignee: Yorker Research Corporation, Woodside, N.Y.

[21] Appl. No.: 755,203

[22] Filed: Dec. 29, 1976

[51] Int. Cl.² .............................................. A24F 25/00
[52] U.S. Cl. .................................................... 239/34
[58] Field of Search ....................... 239/34, 36, 42, 47, 239/55, 57, 56, 58, 145; 206/0.5

[56] References Cited

U.S. PATENT DOCUMENTS

3,856,204  12/1974  Chand .................................... 239/34
3,888,416  6/1975  Lin ......................................... 239/34

Primary Examiner—James B. Marbert
Attorney, Agent, or Firm—Robert T. Tobin

[57] ABSTRACT

The vaporizer is adapted to be worn directly on the person by means of a clip or a chain. The vaporizer includes two chambers which receive suitable vaporizable liquid compounds or mixtures. The upper chamber is opened to the atmosphere via a rotatable cap and plunger assembly for dispensing vapors while the lower chamber can be opened for dispensing of liquid drops upon removal of a threaded cap.

24 Claims, 15 Drawing Figures

PERSONAL AUTOMATIC VAPORIZER

This invention relates to a vaporizer. More particularly, this invention relates to a personal automatic vaporizer.

As is known, various types of vaporizers have been known for generating a vapor for use in a surrounding environment. In some cases, the vaporizers have been constructed to operate under electrical power, for example, in order to vaporize water and, in some cases, mixtures of water and a medicated compound. Vaporizers of this type are frequently used to aid a person's breathing, particularly young children and those with breathing incapacities. However, these vaporizers generally require placement in a fixed position and cannot be readily carried from place-to-place during use.

Various vaporizers have also been known for use as personal vaporizers. In such cases, the vaporizers have been constructed as relatively small containers in which a vaporizable compound or mixture can be carried in a closed condition and which can be opened at suitable times for dispensing. For example, it has been known to use capped bottles to carry a vaporizable compound and to release the vapors of the compound by removing the cap. However, these types of vaporizers have frequently been subject to leakage if the caps are not tightly secured.

In order to prevent leakage, it has also been known to use vaporizing diffusers, such as a perfume container as described in U.S. Pat. No. 2,733,098, which uses cotton or other absorbing material in order to absorb a vaporizable material of liquid, solid or paste form for subsequent diffusion of vapors. However, in such cases, the amount of vapor produced has usually been insufficient to produce the required effect or to produce the required effect over prolonged periods of time. This is due in part to the fact that the liquids can only vaporize from the surface of the absorbing material and in part to the fact that the absorbing material and liquid may change in quality due to chemical reactions therebetween. Further, the known vaporizing materials have generally always included a large portion of starch. This, however, lessens the vaporizing effect and also leaves a large amount of starch as a residue. Also, the personal diffusers have in some cases been bulky and heavy and, as such, cumbersome to carry on the person.

It has also been known to utilize vaporizers which operate on an aerosol principle. However, many objections have been made to the use of aerosols for dispensing purposes.

Accordingly, it is an object of the invention to provide a personal automatic vaporizer which is not subject to leakage.

It is another object of the invention to provide a personal vaporizer which is light in weight.

It is another object of the invention to provide an automatic vaporizer which can be carried on the person in a relatively simple manner.

It is another object of the invention to provide a personal automatic vaporizer which does not rely upon aerosols for operation.

It is another object of the invention to provide a vaporizer which is able to provide a relatively effective vaporizing atmosphere.

It is another object of the invention to provide a personal vaporizer which is efficient and of low cost.

It is another object of the invention to provide a personal vaporizer which provides long lasting effects.

It is another object of the invention to provide a vaporizer which is able to produce vapors and which can be used to dispense scented liquid materials in droplet form.

Briefly, the invention provides a personal automatic vaporizer which is comprised of a housing having a pair of chambers for receiving vaporizing liquids as well as a pair of openings which communicate each of the chambers with the exterior of the housing. In accordance with the invention, at least one of the openings is of a size sufficient to render the total force of surface tension and the attractive force between the liquid in the chamber and the housing wall greater than the weight of the liquid in the chamber. When the housing is disposed so that this chamber is directed downwardly, the liquid will not flow out of the chamber under gravity. Instead, the liquid will be retained.

The principle of preventing leakage from the bottom opening of the housing resides in making the size of the discharge opening so small that the total force of surface tension and the attractive force between the liquid in the chamber and the wall of the chamber is greater than the weight of the liquid. For example, the opening is made of a diameter of 0.075 inches to 0.090 inches. For purposes of illustration, a one ounce glass bottle with an opening of 0.090 inches in diameter which is filled with water will not leak when hanging in an upside down condition unless shaken. Based on this principle, the bottom chamber of the vaporizer is used to dispense liquid drops after being opened and shaken while the upper chamber is used to dispense vapors.

The vaporizer further has a cap which is removably secured to the housing over one discharge opening in order to close the opening as well as a closure means over the other discharge opening in order to selectively open and close the opening.

The closure means is constructed so that the upper chamber can be opened and closed to permit dispensing of vapors. To this end, the closure means includes a plunger in the housing for sealing the discharge opening, a spring which biases the plunger away from the discharge opening, a cap which is rotatably mounted on the housing between a first end position and a second end position and a cam between the cap and the plunger for moving the plunger towards the opening upon rotation of the cap from the first position to the second position. Thus, when the cap is in the first position, the discharge opening is in communication with the exterior of the housing, for example, via suitable windows which are aligned in the housing and cap. However, when the cap is in the second end position, the plunger closes the discharge opening. At the same time, the windows are out of alignment. Thus, the contents, i.e. the vapors in the chamber cannot escape.

As is known, under a fixed temperature and air pressure, any kind of liquid has a determined vaporizing density. However, the vaporizing speed of slow vaporizing liquids, such as oils, fragrances and the like, can be increased by mixing in faster vaporizing liquids such as alcohol. Increasing the temperature of the liquid also increases the vaporization of the liquid. Also, shaking or stirring of the liquid can increase the speed and quantity of vaporization. In the present case, by hanging the vaporizer from the person, such as around a person's neck, the normal body motions will aid in vaporizing the liquids within the upper chamber when the chamber is opened.

The vaporizing liquids which are used may be of any suitable type. In particular, the liquids may be a medicated oil or fragrance or any other suitable vaporizable liquid which is able to impart a sense of freshness and clean atmosphere.

The vaporizer is capable of various uses and applications. For example, the upper chamber can be filled with a cologne or other fragrance which can vaporize automatically and continuously through the aligned windows. Such a vaporizer can be used as a necklace or as a pen-like accessory for wearing on the person. Alternatively, the upper chamber can be filled with a medicated oil to aid breathing or to relieve minor symptoms of colds, hay fever, asthma and the like. The effective time of vaporization can be controlled and adjusted depending on an individual's requirements by differential rotation of the closure cap. For this purpose, the cap may be provided with a reference mark in order to indicate the amount of opening.

The lower chamber of the vaporizer may also be filled with a cologne, a fragrance or a perfume and used in a conventional way. Also, the lower chamber may be filled with an anti-perspirant or a deodorizer which can be applied at any time. Also, the lower chamber may be provided with a breath freshener; or with a medical oil such as German Green oil for first aid or minor cuts; or with a solid menthol inhaler for relieving nasal congestion.

Generally, both chambers can be filled with the same materials or can be filled with different materials.

In addition, the vaporizer can be made to accommodate refill cartridges.

These and other objects and advantages of the invention will become more apparent from the following detailed description and appended claims taken in conjunction with the accompanying drawings in which:

Figures 1, 2, 3, 4:
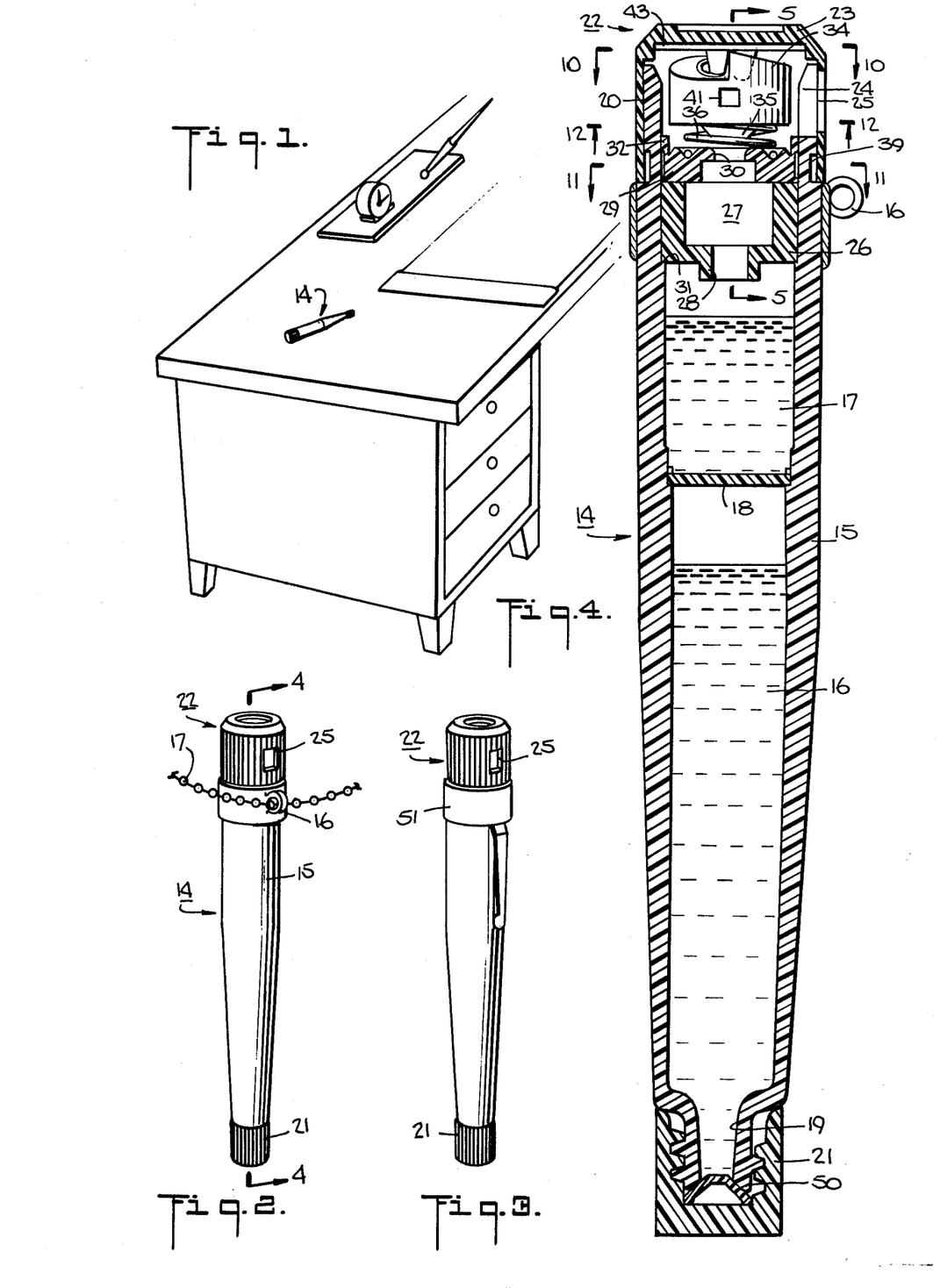
FIG. 1 illustrates a view of a personal automatic vaporizer according to the invention used in open condition on an office desk.
FIG. 2 illustrates an enlarged view of the vaporizer of FIG. 1 without a chain.
FIG. 3 illustrates a modified embodiment of the vaporizer according to the invention used with a clip.
FIG. 4 illustrates a view taken on line 4—4 of FIG. 2.

Referring to FIG. 2, the personal automatic vaporizer 14 is constructed with a housing 15 of elongated generally cylindrical shape and is provided with an eyelet 16 for receiving an endless chain 17 (FIG. 2) so as to be suspended about the neck of a person.

Referring to FIG. 4, the housing 15 has a pair of liquid-filled chambers 16, 17 which are divided by a partition 18. Each of these chambers 16, 17 is of suitable capacity for personal use, e.g. each may have a one ounce capacity. A first discharge opening 19 is located in the housing 15 at the lower end, as viewed, to communicate with the lower chamber 16. The opposite end of the housing has a peripheral wall 20 which defines an opening and which communicates with the chamber 17 at the upper end. As shown in FIGS. 2 and 4, a cap 21 is removably secured, as by threading, to the housing 15 over the discharge opening 19 in order to close the opening 19 and prevent discharge of the liquid in the lower chamber 16. A closure means 22 is also disposed at the upper end of the housing 15 and constitutes, in part, a movable cap 23 which is secured to the housing 15 over the opening. This closure means 22 serves to selectively open and close the opening.

Figures 7, 8, 9:
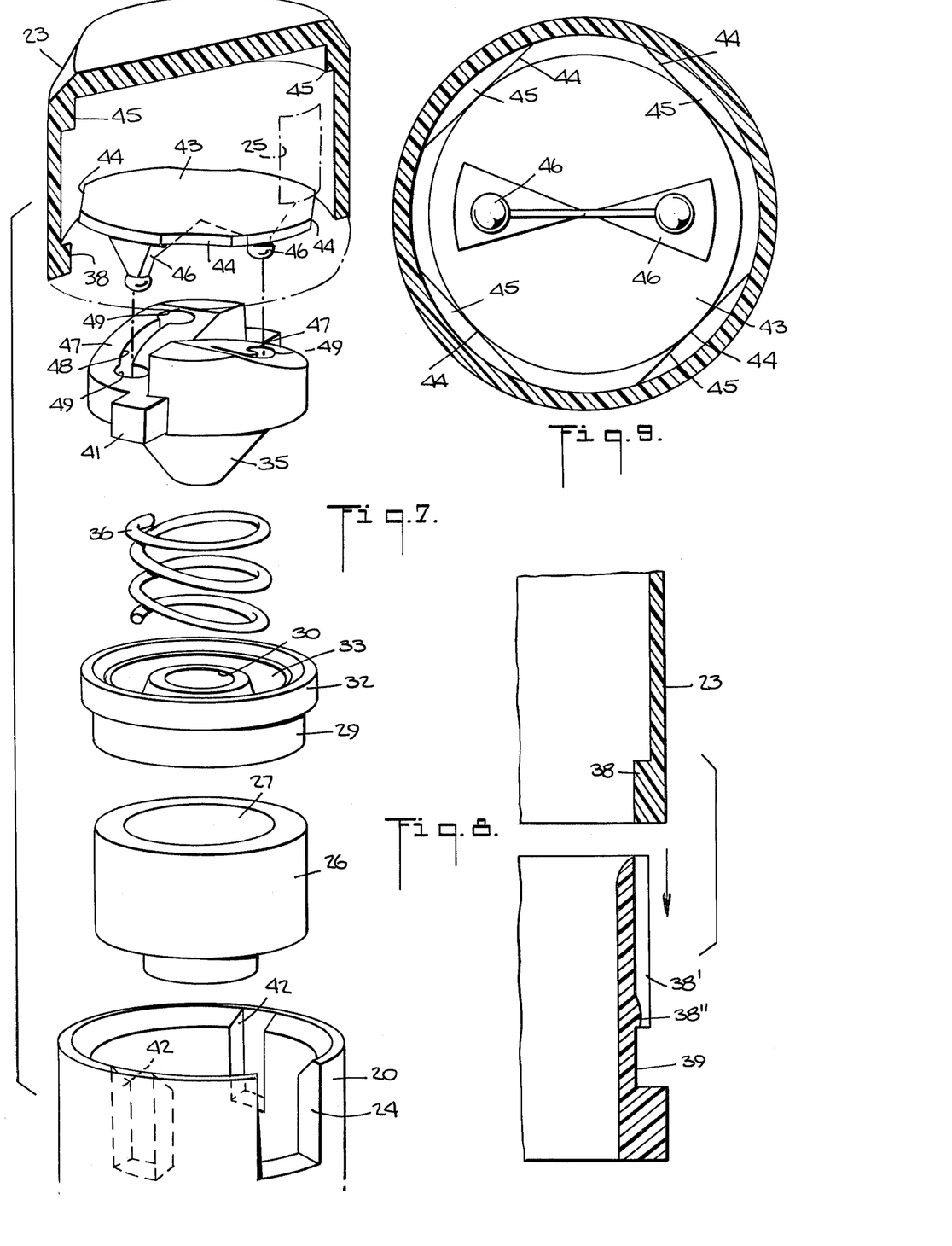
FIG. 7 illustrates an exploded view of the upper end of the vaporizer of FIG. 4.
FIG. 8 illustrates a fragmentary exploded view of the closure cap and housing of the vaporizer according to the invention.
FIG. 9 illustrates a view taken on line 9—9 of FIG. 6 of the cam according to the invention.

Referring to FIGS. 4 and 7, the upper end of the housing peripheral wall 20 has a window 24 which is defined by a slot to communicate with the interior of the housing and the cap 23 has a window 25 which is adapted to be aligned with the window 24 in the wall 20.

Figure 5:
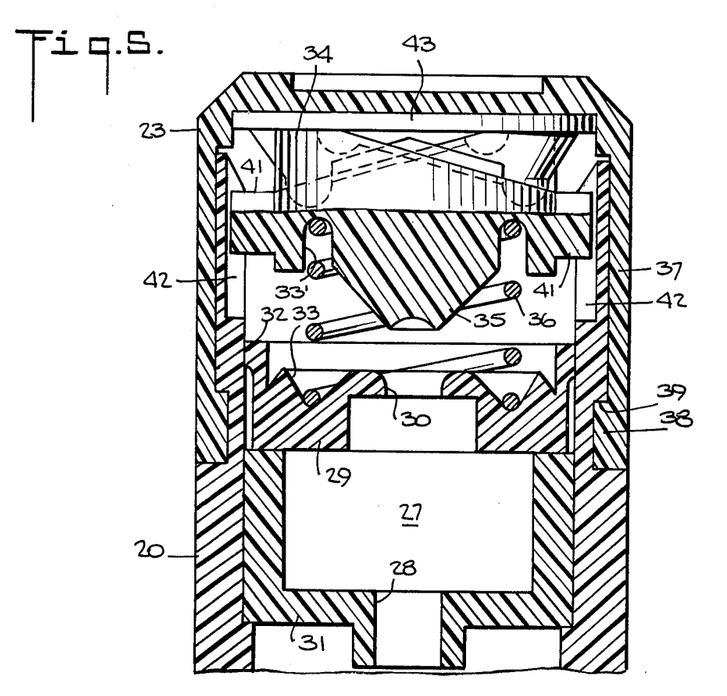
FIG. 5 illustrates a view taken on line 5—5 of FIG. 4.

Referring to FIGS. 4, 5 and 7, an insert 26 is mounted within the opening of the housing 15 above the upper chamber 17 in order to form a vaporization chamber 27 spaced from the liquid receiving chamber 17. This insert 26 has a central discharge opening 28 which communicates the vaporization chamber 27 with the liquid receiving chamber 17 of the housing 15. Also, a disc 29 is mounted on the insert 26 and has a discharge opening 30 communicating with the vaporization chamber 27. This disc 29 is made up of elastic material or any other suitable yieldable material so as to sealingly seat on the housing wall 20. As shown, the insert 26 seats on a shoulder 31 of the housing wall 20 while the disc 29 serves to lock the insert 26 in place. To this end, the insert 26 has an annular elastic seal 32 which prevents air and liquid leakage and which seats against the housing wall 20 with a slight friction fit. In addition, the disc 29 has an annular groove 33 in the upper surface about the discharge opening.

The closure means 22, in addition to the cap 23, includes a plunger 34 which is mounted within the housing 15 and which has a portion 35 for sealingly seating in the discharge opening 30 of the disc 29. This plunger 34 also has an annular groove 33 (FIG. 5) opposite the groove 33 of the disc 29 in which a spring 36 is located to bias the plunger 34 away from the disc 29.

As shown, the closure cap 23 is rotatably mounted on the housing 15 over and about the peripheral wall 20. This cap 23 has a skirt portion 37 on which two bosses 38 are mounted at a lower end to project inwardly. These bosses 38 fit into an annular groove 39 on the exterior of the housing wall 20 and as such, serve to prevent loosening of the cap 23 from the housing 15 while at the same time permitting rotation of the cap 23 relative to the housing 15. As shown in FIG. 8, the exterior of the housing wall 20 is provided with two vertical grooves 38' in which the bosses 38 can slide during assembly of the vaporizer. Each groove 38' also has an inclined cam surface 38" over which a boss 38 slides into the annular groove 39. These cam surfaces 38" serve to lock the cap 23 in place.

Figures 10, 11, 12, 13:
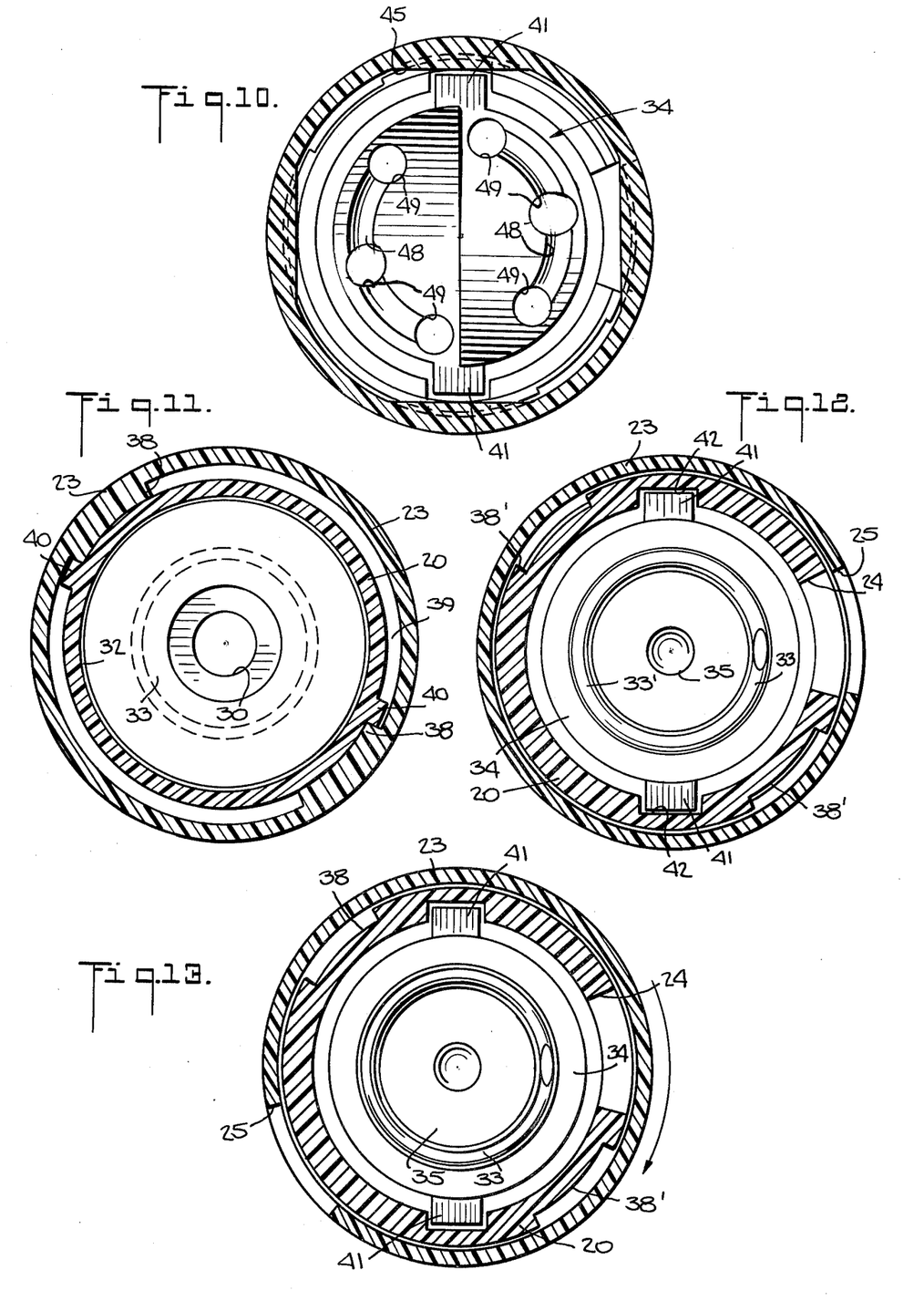
FIG. 10 illustrates a view taken on line 10—10 of FIG. 4 of the plunger according to the invention.
FIG. 11 illustrates a view taken on line 11—11 of FIG. 4.
FIG. 12 illustrates a view taken on line 12—12 of FIG. 4.
FIG. 13 illustrates a view similar to FIG. 12 of the vaporizer in a closed condition.

As shown in FIG. 11, a pair of projections 40 are diametrically disposed within the annular groove 39 in order to act as stops against rotation of the cap 23 on the housing 20. These projections 40 engage against the bosses 38 when the cap 23 is moved from a first position (i.e. an open position) wherein the liquid receiving chamber 17 and the vaporization chamber 27 are in communication with the exterior of the housing via the windows 24, 25 and a second position (i.e. a closed position) wherein the windows 24, 25 are out of alignment and the plunger 34 seats on the disc 29 to close the discharge opening 30.

As shown in FIGS. 5 and 7, the plunger 34 contains a pair of protuberances 51 which are diametrically opposed and which matingly seat within two diametrically opposed vertical grooves 42 in the housing wall 20. These vertical grooves 42 and cooperating protuberances 41 permit the plunger 34 to slide vertically within the housing 15.

Referring to FIGS. 4, 5 and 7, the closure means 23 also includes a cam 43 between the cap 23 and the plunger 34 for moving the plunger 34 towards the disc 29 upon rotation of the cap 23 from the open position to the closed position. This cam 43 is of disc-like construction and is seated within the interior of the cap 23. As shown in FIG. 9, the cam 43 is provided with a plurality of flats 44, e.g. four, which cooperate with abutments 45 on the interior of the cap 23 so that the cam 43 is non-rotatably mounted within the cap 23. In addition, the cam 43 has a pair of nipples 46 which project outwardly. These nipples 46 are disposed in diametric fashion and cooperate with inclined cam surfaces 47 on the top of the plunger 34 (FIG. 7) which are oppositely inclined from each other for sliding of the nipples 46 thereon. As shown in FIG. 10, the plunger 34 has a pair of arcuate grooves 48 in the cam surfaces 47, each of which receives a respective nipple 46 therein. In addition, each groove 48 has a recess 49 at each end for matingly locking the respective nipple 46 therein. As shown, the nipples 46 are provided with a rounded end so as to easily slide on the cam surfaces 47 of the plunger 34.

Referring to FIG. 4, the cap 21 at the lower end of the housing 20 includes a seat 50 for sealing against the discharge opening 19.

The vaporizer is used in the following manner.

Figure 6:
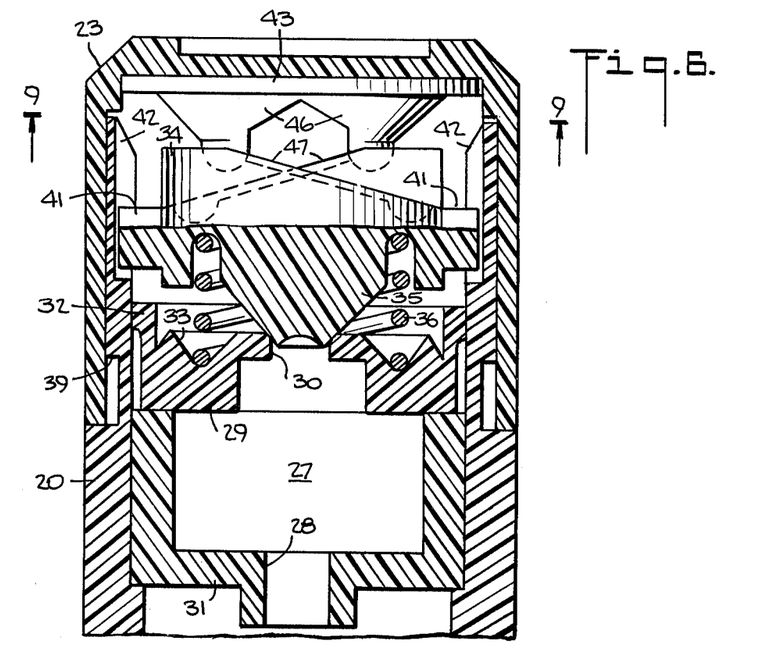
FIG. 6 illustrates a view similar to FIG. 5 of the upper chamber of the vaporizer in a closed position.

Referring to FIG. 4, when the upper chamber 17 is opened, the liquid within the chamber 17 is able to vaporize and pass vapors through the vaporization chamber 27 and aligned windows 24, 25 into the surrounding atmosphere. In order to close the vaporizer 14, the cap 23 is rotated on the housing 15, for example from the position shown in FIGS. 11 and 12 to the position shown in FIG. 13. In this latter position, the windows 24, 25 are out of alignment with each other, the cap 23 having been turned slightly less than 180°. At the same time, as shown in FIG. 6, the cam 43 has moved the plunger 34 downwardly against the disc 29 so that the plunger portion 35 closes the discharge opening 30 for the vaporization chamber 27. At this time, the spring 36 is in a compressed position. Also, at this time the nipples 46 of the cam 43 lock within the respective recesses 49 of the plunger 34. Still further, the inwardly directed bosses 38 of the cap 23 have rotated to a position abutting against the stops 40 on the housing wall 20 so that continued rotation is no longer possible.

In order to reopen the upper chamber 17, the cap 23 is rotated in a counterclockwise direction from that as viewed in FIG. 13 until the two windows 24, 25 of the cap 23 and housing 15 are aligned. During this time, the nipples 46 of the cam 43 move along the inclined surfaces of the plunger 34 while the spring 36 urges the plunger 34 upwardly as viewed in FIG. 6 into the position shown in FIG. 5. During this time, the plunger 34 slides within the vertical grooves 42 of the housing wall 20.

The cap 23 may be rotated into a partially opened condition in order to reduce the amount of vapor being dispensed. For this purpose, the cam 43 may be provided with a reference mark on the upper surface while the cap 23 is made of transparent material so that the reference mark can be viewed. Alternatively, as viewed in FIG. 10, additional recesses 49' may be provided in the cap 23 intermediately of the recesses 49 to receive the nipples 46 of the cam 43. Also, since the cam 43 and cap 23 are fixed relative to each other, a reference mark can be made on the cap 23 to indicate the position of the cam 43.

Referring to FIG. 3, the vaporizer may also be provided with a clip 51 so as to permit wearing on the person in the form of a pen.

Any suitable vaporizable liquid may be charged into the upper chamber 17 and likewise any suitable medium may be charged into the lower chamber 16. To this end, the liquids may be selected from the group consisting of perfume, cologne, fragrances, medicated oils and deodorizers. Further, the lower chamber 16 may be filled with solid menthol inhalers.

The diameter of the discharge openings 19, 28, 30 in the lower end of the housing 15, the insert 26 and the disc 29 are made of a diameter of from 0.075 to 0.090 inches. In this way, the liquid in the lower chamber 16 is not able to flow outwardly under gravity since the surface tension and attractive forces between the liquid and the housing is greater than the force of the weight of the liquid. Thus, with the cap 21 removed, the liquid will not flow out of the discharge opening unless the vaporizer 14 is shaken. Similarly, the vaporizer 14 may be shaken so that the liquid in the upper chamber 17 can be dispensed in droplet form provided the closure means 22 is in an open condition.

The housing 15 can be made of any suitable material such as a lightweight plastic and the other components of the vaporizer may also be made as of any suitable lightweight materials. In this way, the vaporizer can be conveniently worn about the neck of a person or can be used in offices, schools and homes by being placed, e.g. on a desk as shown in FIG. 1.

During use, it has been found that a vaporizer constructed in the above manner can hold and vaporize a German Green oil or a menthol medicated oil for about 2 months. In this case, the chamber 17 is of one ounce capacity with a discharge opening 28, 30 of 0.090 inches. The same vaporizer in vaporizing colognes, fragrances or perfumes has been found to hold approximately one month when the windows 24, 25 are kept open 4 hours per day for regular items, (i.e. 70% SDA 39C 190). For weaker items (80% SDA 39C 190), the vaporizer 14 can hold approximately 1 month when the windows 24, 25 are kept open 8 hours per day.

Figure 14:
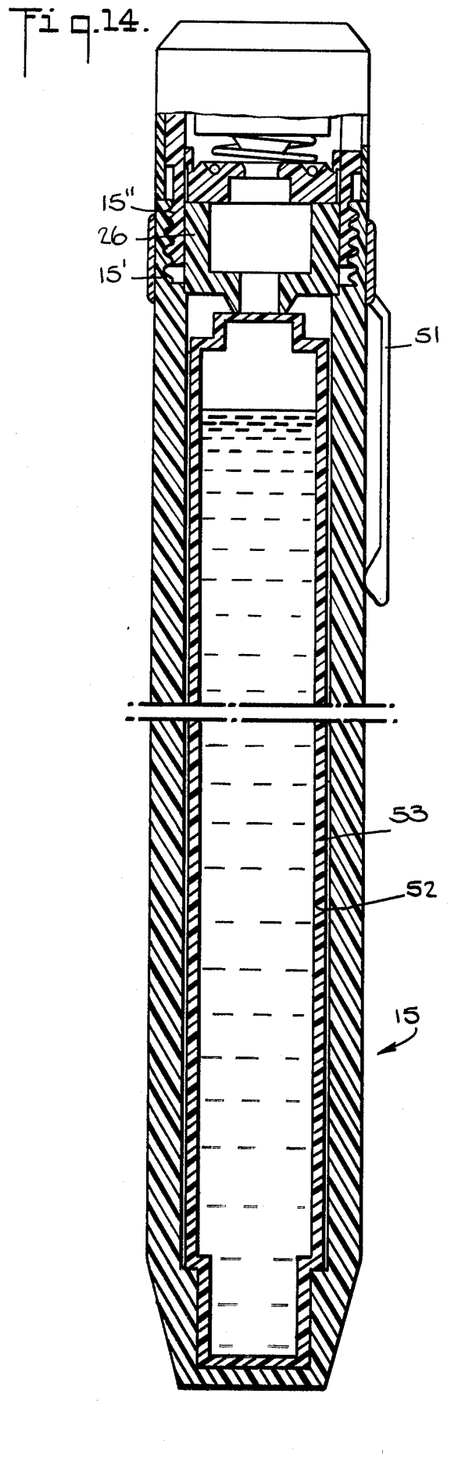
FIG. 14 illustrates a cross-sectional view of a refillable vaporizer in accordance with the invention.
Figure 15:
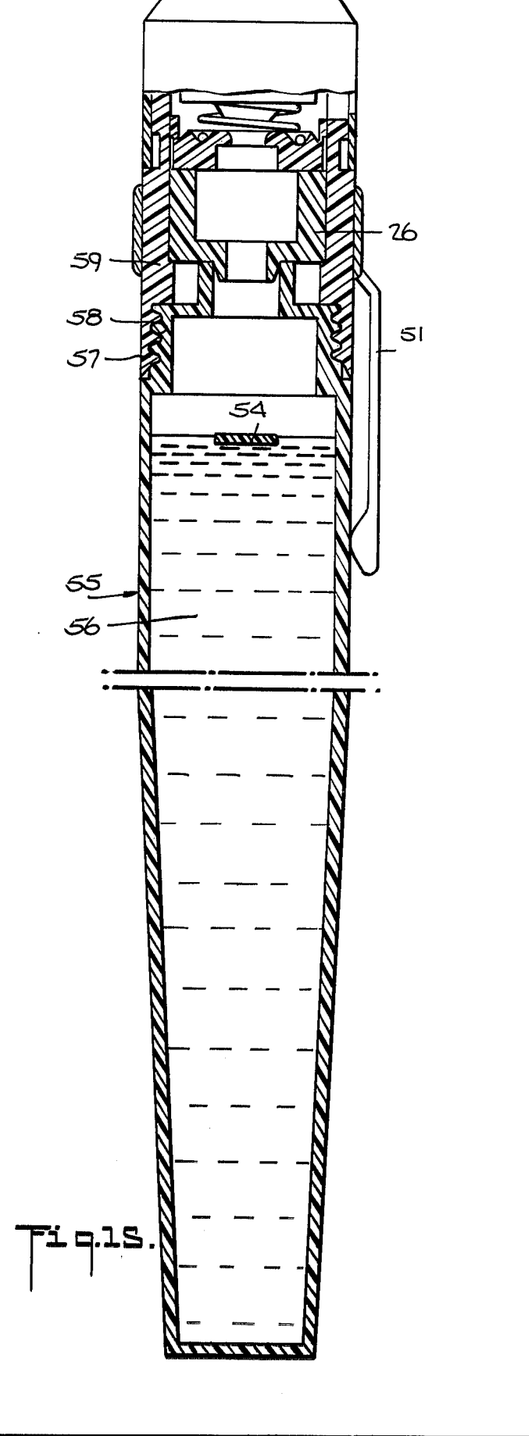
FIG. 15 illustrates a view similar to FIG. 14 of another vaporizer of the re-fill type according to the invention.

Various modifications can, of course, be made in the vaporizer. For example, as shown in FIGS. 14 and 15, wherein like reference characters indicate like parts as above, the housing may define a single chamber 52 into which a removable cartridge 53 containing one or more chambers for vaporizable liquids can be placed and which can be changed from time to time. In this case, the refill cartridge 53 has a single chamber to which access is made through a rupturable seal 54 at the end adjacent the insert 26. The housing 15 is also formed of two threaded sections 15', 15" so that tightening of the two sections of the housing 15 on each other causes the cartridge 53 to move against the insert 26 to break open the seal 54. When the seal 54 is removed, the cartridge 53 seals tightly against the discharge opening 28 of the insert 26 to prevent leakage. Operation of the vaporizer is similar to the above described vaporizer of FIG. 4.

As shown, the lower end of the cartridge 53 is narrowed to mate with a corresponding restriction in the housing 15. This prevents the cartridge 53 from slipping away from the housing 15.

Referring to FIG. 15, wherein like reference characters indicate like parts as above, the vaporizer may be formed with a cartridge 55 having a single chamber 56 with a rupturable seal 54 at the upper end, as viewed. In this case, the upper end of the cartridge 55 is provided with an external screw thread 57 to threadably engage an internal screw thread 58 on a housing 59 in which an insert 26 is mounted in a manner as described in FIG. 4. As shown, the housing 59 is shorter than the above described housing 15.

In operation, the cartridge 55 is initially threaded into the housing 59 until the seal 54 abuts the insert 26. Continued threading causes the seal 54 to rupture as shown. Next, in order to open the chamber 56 to the outside, the cap 23 is rotated in a manner as described above.

The invention thus provides a personal vaporizer which is capable of automatically dispensing scents or vapors without the use of aerosols. The vaporizer may be embodied in housings of various shapes and sizes so as to impart an aesthetic appearance when worn on the person in an exposed manner.

Further, vapor can flow out of the vaporizer directly without the need for cotton or other similar absorbent material to prevent leakage. In addition, the cap 23 may be provided with more than one window.

What is claimed is:

1. A personal automatic vaporizer comprising
a housing having a pair of chambers for receiving respective vaporizing liquids therein, said housing having a first discharge opening communicating one of said chambers with the exterior of said housing, and a second discharge open communicating the other of said chambers with the exterior of said housing,
at least said first opening being of a size sufficient to render the total force of surface tension and the attractive force between the liquid in said first chamber and said housing greater than the weight of the liquid in said first chamber,
a cap removably secured to said housing over said first discharge opening to close said first discharge opening, and
a movable cap secured to said housing over said second discharge opening to selectively open and close said second discharge opening.

2. A personal automatic vaporizer as set forth in claim 1 wherein each of said discharge openings are of a diameter from 0.075 inches to 0.090 inches.

3. A personal automatic vaporizer as set forth in claim 1 which further comprises a plunger in said housing for sealing said second opening, a spring biasing said plunger away from said second opening, a cap rotatably mounted on said housing between a first end position and a second end position and a cam between said cap and said plunger for moving said plunger towards said second opening upon rotation of said cap from said first position to said second position whereby in said first position said second discharge opening is in communication with the exterior of said housing and in said second position said plunger closes said second discharge opening.

4. A personal automatic vaporizer as set forth in claim 3 wherein said cam is rotatably fixed to said cap.

5. A personal automatic vaporizer as set forth in claim 3 wherein said housing has a first window communicating with said second discharge chamber and said cap has a second window for selectively communicating with said first window upon movement of said cap to said first position.

6. A vaporizer comprising
an elongated housing having a pair of chambers therein, a first discharge opening at one end communicating with one of said chambers, a peripheral wall defining an opening at the opposite end, and a window in said wall;
a cap removably secured to said housing at said one end to seal said first discharge opening;
an insert mounted within said opening at said opposite end to form a vaporization chamber spaced from said chambers and having a discharge opening communicating said vaporization chamber with the other of said pair of chambers;
a disc mounted on said insert and having a discharge opening communicating with said vaporization chamber,
a plunger having a portion for sealingly seating in said opening of said disc;
a spring between said plunger and said disc for biasing said plunger away from said disc;
a closure cap rotatably mounted on said housing over and about said peripheral wall and having a window for selective alignment with said window in said housing wall; and
a cam between said cap and said plunger for moving said plunger towards said disc upon rotation of said cap from a position wherein said windows are aligned to permit discharge of a vapor to a position wherein said windows are out of alignment to prevent discharge of a vapor.

7. A vaporizer as set forth in claim 6 wherein said housing of hollow and of substantially cylindrical shape.

8. A vaporizer as set forth in claim 7 which further includes a partition between said liquid receiving chambers.

9. A vaporizer as set forth in claim 6 wherein said insert is made of elastic material.

10. A vaporizer as set forth in claim 6 wherein said cam is secured to said closure cap for rotation therewith.

11. A vaporizer as set forth in claim 10 wherein said cam has a pair of nipples projecting therefrom and said plunger has a pair of oppositely inclined cam surfaces for sliding of said nipples thereon.

12. A vaporizer as set forth in claim 11 wherein said plunger has a pair of arcuate grooves, each said groove receiving a respective nipple therein and having a recess at one end for matingly locking said respective nipple therein.

13. A vaporizer as set forth in claim 12 wherein said plunger is slidably mounted in said peripheral housing wall and said cam is rotatable relative to said plunger.

14. A vaporizer as set forth in claim 6 which further comprises a seal in said cap at said one end for sealing said opening thereat.

15. A vaporizer as set forth in claim 6 which further comprises a clip mounted on said housing about said peripheral wall.

16. A vaporizer as set forth in claim 6 which further comprises an eyelet on said housing for receiving an endless chain therein.

17. A vaporizer as set forth in claim 6 wherein each of said pair of chambers is filled with a vaporizable liquid.

18. A vaporizer as set forth in claim 17 wherein said liquid is selected from the group consisting of perfume, cologne, fragrances, medicated oils, deodorizers.

19. A vaporizer as set forth in claim 6 wherein one of said pair of chambers is filled with a solid menthol inhaler.

20. A vaporizer as set forth in claim 6 wherein each of said discharge opening is of a diameter of from 0.075 to 0.090 inches.

21. A closure means for a housing having a peripheral wall defining a chamber and having a window in said wall, said closure means comprising
   a disc mounted in said housing on said wall and over said chamber and having a discharge opening therein,
   a plunger having a portion for sealingly seating in said opening of said disc;
   a spring between said plunger and said disc for biasing said plunger away from said disch;
   a closure cap rotatably mounted on said housing over and about said peripheral wall and having a window for selective alignment with said window in said housing wall;
   a cam between said cap and said plunger for moving said plunger towards said disc upon rotation of said cap from a position wherein said windows are aligned to permit discharge of the contents of said chamber to a position wherein said windows are out of alignment to prevent discharge of the contents of said chamber.

22. A vaporizer comprising
   an elongated housing having a chamber therein, a peripheral wall defining a discharge opening at one end of said chamber, and a window in said wall;
   an insert mounted within said opening at said end to form a vaporization chamber spaced from said first chamber and having a discharge opening communicating said vaporization chamber with said first chamber;
   a disc mounted on said insert and having a discharge opening communicating with said vaporization chamber;
   a plunger having a portion for sealingly seating in said opening of said disc;
   a spring between said plunger and said disc for biasing said plunger away from said disc;
   a closure cap rotatably mounted on said housing over and about said peripheral wall and having a window for selective alignment with said window in said housing wall; and
   a cam between said cap and said plunger for moving said plunger towards said disc upon rotation of said cap from a position wherein said windows are aligned to permit discharge of a vapor to a position wherein said windows are out of alignment to prevent discharge of a vapor.

23. A vaporizer as set forth in claim 22 which further comprises a removable cartridge in said housing defining said first chamber for a vaporizable liquid.

24. A vaporizer as set forth in claim 23 wherein said cartridge has a rupturable seal opposite said insert.

* * * * *

UNITED STATES PATENT AND TRADEMARK OFFICE
CERTIFICATE OF CORRECTION

PATENT NO. : 4,106,698
DATED : August 15, 1978
INVENTOR(S) : A. Oscar Lin

It is certified that error appears in the above–identified patent and that said Letters Patent are hereby corrected as shown below:

Column 5, line 19, change "51" to -- 41 --;

*Signed and Sealed this*

*Twenty-seventh* Day of *March 1979*

[SEAL]

Attest:

RUTH C. MASON
*Attesting Officer*

DONALD W. BANNER
*Commissioner of Patents and Trademarks*